US005515234A

United States Patent [19]
Frazier

[11] Patent Number: 5,515,234
[45] Date of Patent: May 7, 1996

[54] ANTISTATIC PROTECTOR AND METHOD

[75] Inventor: Gary A. Frazier, Garland, Tex.

[73] Assignee: Texas Instruments Incorporated, Dallas, Tex.

[21] Appl. No.: 86,276

[22] Filed: Jun. 30, 1993

[51] Int. Cl.⁶ .............................. H01J 39/06; H01J 39/16
[52] U.S. Cl. .............................................. 361/212; 361/220
[58] Field of Search .................................. 361/212, 220, 361/223, 224, 229, 230, 231, 232; 307/4.1, 10.1; 29/825, 857; 330/3, 277; 313/309, 336, 351, 54

[56] References Cited

U.S. PATENT DOCUMENTS 3,814,968  6/1974  Nathanson et al. ...................... 313/95
4,402,560  9/1983  Swainbank ............................... 339/11
4,745,519  5/1988  Breidegam .............................. 361/220
4,849,851  7/1989  Cubbison, Jr. ........................... 361/212
5,083,367  1/1992  Klepel ...................................... 29/825
5,179,497  1/1993  Bakhoum ................................. 361/212

FOREIGN PATENT DOCUMENTS 2513060  9/1981  France .............................. H05F 3/04
8909479  10/1989  France .

*Primary Examiner*—Peter S. Wong
*Assistant Examiner*—Adltya Krishnan
*Attorney, Agent, or Firm*—Carlton H. Hoel; W. James Brady, III; Richard L. Donaldson

[57] ABSTRACT

An electrostatic discharge system (100) worn on an individual's wrist includes an array of field emitters (102) to discharge built up electrostatic charge on the individual into ambient air.

17 Claims, 5 Drawing Sheets ns,234

ANTISTATIC PROTECTOR AND METHOD

BACKGROUND OF THE INVENTION

This invention relates to electronic devices, and, more particularly, to electrostatic discharge protection devices and methods.

Many electronic components, such as integrated circuits, MOS transistors, diodes, and thin film capacitors are sensitive to electrostatic discharge (ESD) and may be damaged during handling. Indeed, the gate oxide in CMOS integrated circuits may be on the order of 200 Å thick and will breakdown at 15–20 volts between the gate and the transistor substrate. Of course, this 15–20 volts greatly exceeds the normal operating voltage, and built-in ESD protection may prevent damage from somewhat higher voltages transiently applied to integrated circuit package pins. But, during handling, electrostatic buildup on a person walking across a room can easily reach 15,000 to 20,000 volts. This high voltage arises from the electric charge generated by rubbing two dissimilar materials together (triboelectric charging effect). The discharge of triboelectric charge into the pins of a packaged transistor or integrated circuit may damage the circuit sufficiently to cause immediate failure or to weaken the circuit to cause subsequent early failure. And on-chip ESD protection devices do not provide sufficient protection without overly encumbering the electrical characteristics (i.e., protection diodes introduce capacitance and protection resistors add to RC time delays).

One approach to providing ESD protection employs conductive clothing for individuals handling ESD sensitive items plus conductive grounded wrist straps and ground mats for discharging accumulated electrostatic charge. However, this approach has problems including the expense of providing electrically conductive clothing or walkways and the ambulatory limits imposed by wrist strap tethering.

SUMMARY OF THE INVENTION

The present invention provides an electrostatic charge dissipator for direct attachment to an individual and employing cold field emission.

BRIEF DESCRIPTION OF THE DRAWINGS

The drawings are schematic for clarity.

DESCRIPTION OF THE PREFERRED EMBODIMENTS

First preferred embodiment overview

Figure 1:
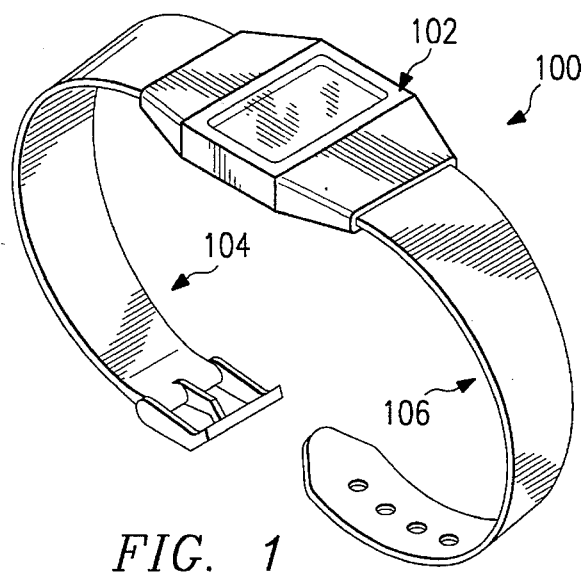
FIG. 1 shows in perspective view first preferred embodiment electrostatic charge dissipation system.
Figure 2:
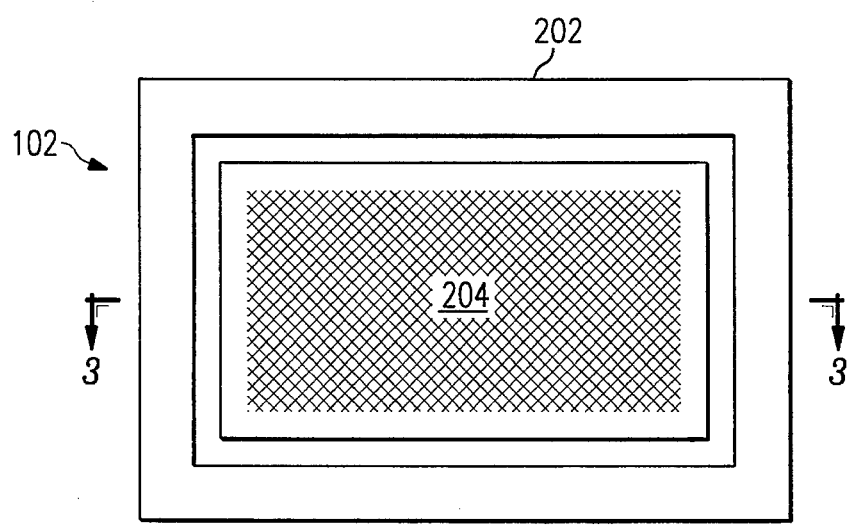
FIGS. 2–3 are plan and cross sectional elevation views of the first preferred embodiment charge dissipator.
Figure 3:
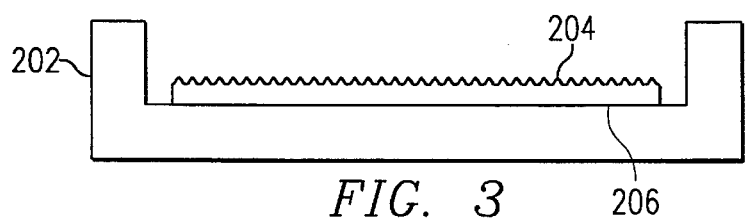

FIG. 1 shows in perspective view first preferred embodiment electrostatic charge dissipation system, generally denoted by reference numeral 100, as including charge dissipator 102 with attached wrist band pieces 104 and 106. Charge dissipator 102 has the dimensions of a small wrist watch, and an individual wears system 100 in the same manner as a wrist watch. FIGS. 2 and 3 show charge dissipator 102 in plan and cross sectional elevation views, respectively, which includes holder 202, made of a conductive plastic such as carbon-doped polyethylene or polyvinyl chloride, with a recess containing silicon emitter array 204 glued with conductive epoxy 206 to holder 202. Emitter array 204 may have the dimensions of 10 mm by 10 mm. The exposed surface of emitter array 204 contains roughly four million field emission emitters, and system 100 operates heuristically as follows.

Electrostatic charge built up on an individual wearing system 100 migrates to the field emission emitters on array 204 and generates high electric fields. These electric fields effectively narrow the potential barrier for electron transport from the emitters into the ambient air. And electrons can tunnel through the sufficiently narrowed barrier to dissipate built up charge. The barrier narrowing depends upon the electric field magnitude which, in turn, depends upon the voltage built up on the individual wearing system 100 and the sharpness of the emitter tips. Thus, the charge dissipation rate increases with the individual's voltage and provides a son of clamping of the individual's relative electrostatic potential to a safe level. And the motion of the individual's wrist during activities such as handling integrated circuits insures ambient air mixing and avoidance of charged air screening and loss of emission efficiency.

Emitter array

Figure 4:
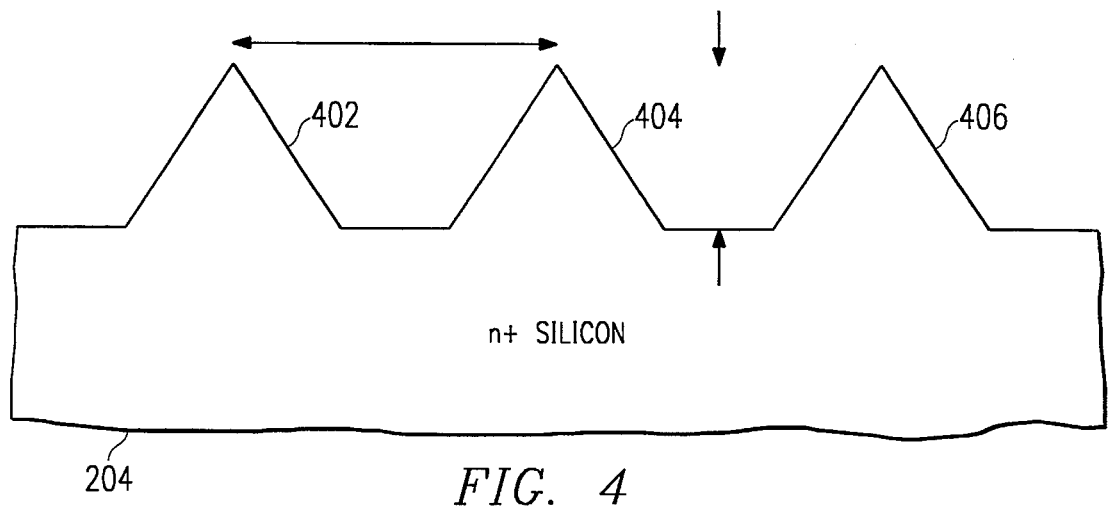
FIG. 4 is an enlarged cross sectional elevation view of the first preferred embodiment charge dissipator.
Figure 5A:
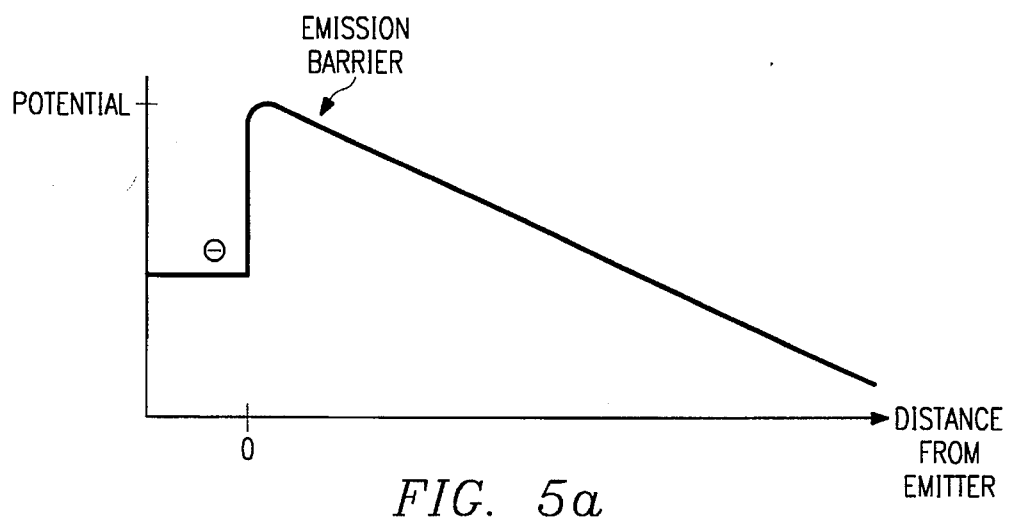
FIGS. 5a–b illustrate electron emission.
Figure 5B:
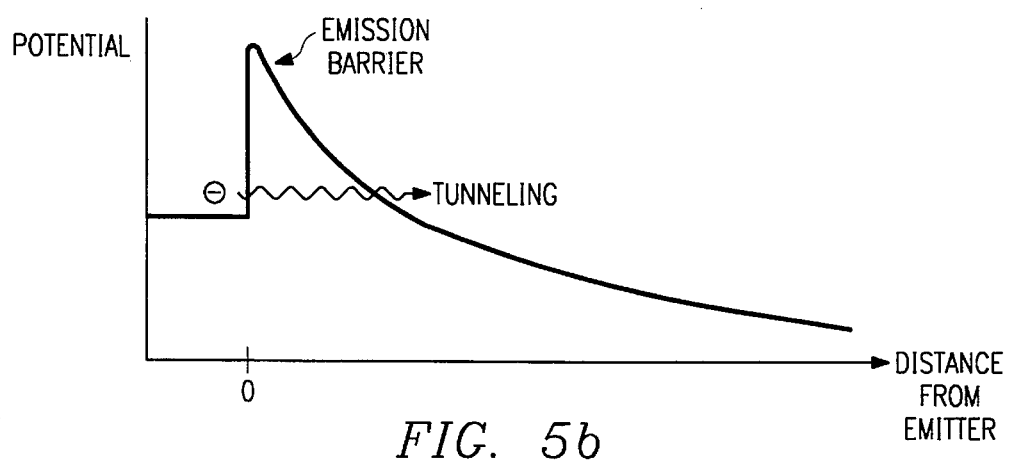

FIG. 4 shows in cross sectional elevation view an enlarged portion of array 204 containing projecting pyramids 402–406 and made of heavily-doped (n+) silicon. The pyramids form an array of rows and columns with a spacing of roughly 5 μm, and each pyramid has a height of roughly 5 μm and a tip curvature on the order of 2 nm. With a tip curvature of 2 nm, a voltage differential of 500 volts between the tip and ambient air will produce an electric field of roughly $4 \times 10^6$ volts/cm at the tip and rapidly falling off from the tip. A sharp tip effectively increases the electric field close to the tip and decreases the electric field away from the tip because the electric field is the gradient of the potential (voltage). FIGS. 5a–b illustrate this change in electric field (slope of potential curve) between a flat emitter (FIG. 5a) and a sharp tipped emitter (FIG. 5b). The potential barrier to electron emission from the emitter tips into the ambient air derives from the work function of the silicon (roughly 5 volts), and electron emission occurs when the high electric field has narrowed the barrier so that electrons can tunnel through the barrier as suggested by the wavy line in FIG. 5b. Of course, this presumes that the individual wearing system 100 is negatively charged with respect to the ambient air and ground.

When an individual wearing system 100 acquires a positive charge with respect to the ambient air and ground, then minority carrier holes accumulate on the emitter tips and can be neutralized by electrons provided by the ambient air. To extract electrons from the ambient air, the electric field about the emitter tips must be sufficiently large to ionize air molecules to generate free electrons. Oxygen and nitrogen will begin to ionize in electric fields on the order of $10^5$ volts/cm, and impact ionization by stray electrons can occur in electric fields as low as $10^3$ volts/cm.

Fabrication

Figure 6A:
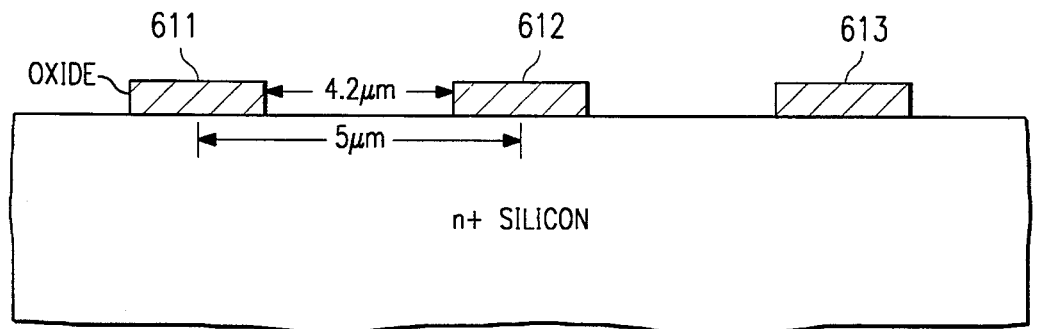
FIGS. 6a–c show fabrication steps in enlarged cross sectional views.
Figure 6B:
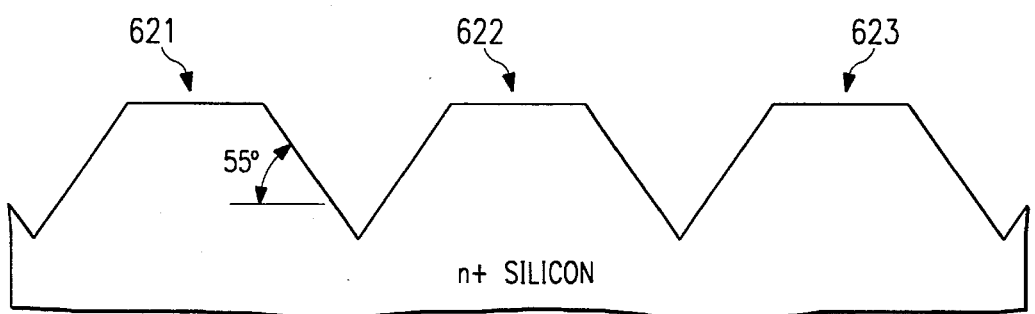
Figure 6C:
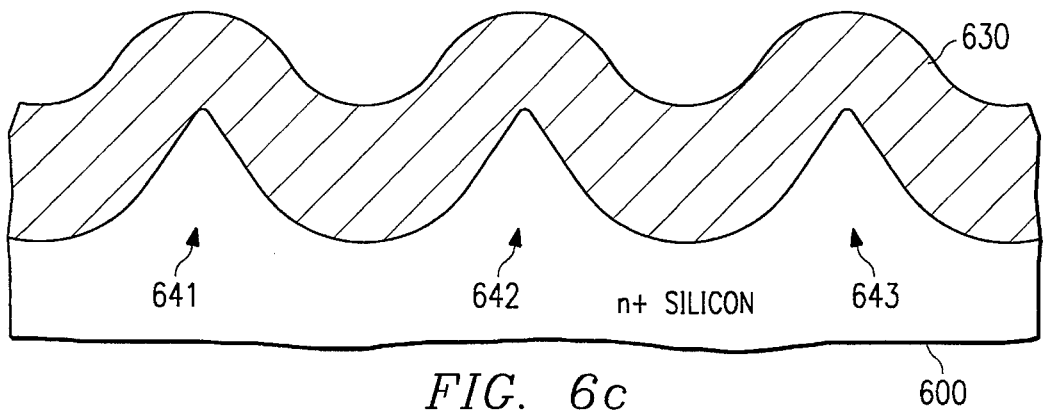

Emitter array 204 may be fabricated in many ways. For example, FIGS. 6a–c show in cross sectional elevation view the following fabrication steps.

(a) Begin with a six-inch diameter n+ silicon wafer 600 having (100) orientation and grow an oxide (silicon dioxide) layer of thickness about 1000 Å. Spin on photoresist and expose and develop a pattern in the photoresist which consists of an array of small squares (2 µm by 2 µm) spaced about 3 µm apart and with sidewalls parallel to {110} planes which includes the standard wafer flat for (100) wafers. Etch the exposed oxide with buffered HF using the patterned photoresist as etch mask; then strip the photoresist. There will be some undercutting and the resultant oxide will be an array of small squares of side about 0.8 µm and spaced about 4.2 µm apart. See FIG. 6a showing oxide squares 611–613.

(b) Etch the exposed silicon 600 with an orientation dependent etch (ODE) such as an aqueous solution of KOH and isopropyl alcohol at 80° C. This etch solution etches {111} very slowly and yields small mesas under the oxide squares 611–613. The mesas have {111} faces and height dependent upon the lateral separation. The corners of the mesas may be somewhat rounded with {331} facets. The mesa faces make an angle of about 55° with the (100) surface. See FIG. 6b showing mesas 621–623.

(c) Thermally oxidize the mesas to form oxide 630 with underlying pyramids 641–643. Oxide 630 has a thickness of roughly 0.5 µm. Dry thermal oxidation provides pyramids 641–643 with sharp tips due to the reduction in oxidation rate at corners arising from the uniaxial oxidation strain. See FIG. 6c.

(d) Lastly, remove oxide 630 with a buffered HF etch. This yields the array as shown in FIG. 4. Then saw substrate 600 into dice (arrays), select an array 204 and glue it with conductive epoxy into holder 202 with wrist straps 104–106 to complete system 100. If necessary to achieve a good electrical contact, the backside of substrate 600 can be coated with gold (0.1 µm thick) and annealed at 400° C. for 15 seconds, before affixing the substrate or die to holder 202.

Figure 7:
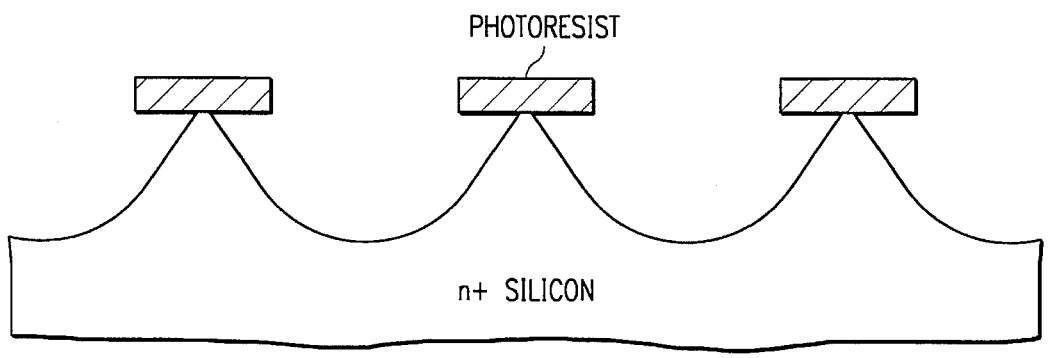
FIG. 7 shows a second fabrication method.

Alternative methods of fabrication include using a timed isotropic etch in step (b). The etchant could be an aqueous solution of $HNO_3$ and HF. This will form rounded pyramids as illustrated in FIG. 7. In this case the patterned oxide can be eliminated and only patterned photoresist used as the etch mask. Again, a dry thermal oxidation may be used to sharpen the pyramid tips.

Different approaches to fabrication of arrays of emitters include growth of silicon whiskers and sharpening the whiskers by oxidation; see Givargizov, Ultrasharp tips for field emission application, 11 J.Vac.Sci.Tech.B 449 (1993).

Second preferred embodiment

Figure 8:
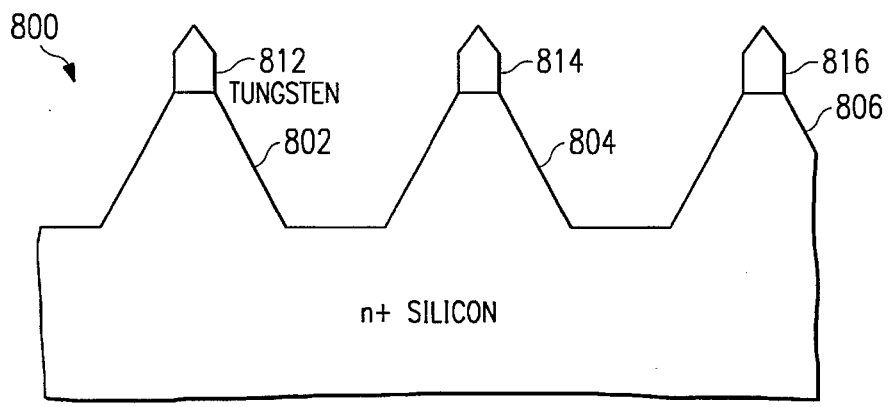
FIG. 8 is an enlarged cross sectional elevation view of a second preferred embodiment charge dissipator.

FIG. 8 shows second preferred embodiment emitter array 800 in cross sectional elevation view. Array 800 is similar to array 204 but with silicon pyramids 802, 804, 806, . . . having flat tops and tungsten tips 812, 814, 816, . . . providing the sharp tip for high electric fields. As with array 204, pyramids 802, 804, 806, . . . are spaced about 5 µm apart and are about 5 µm high. Tungsten tips 812, 814, 816, . . . have a square base with edge about 1 µm and are about 1 µm high with tip curvature on the order of 2 nm. System 100 can use array 800 in place of array 204 and operate in the same manner.

Figure 9A:
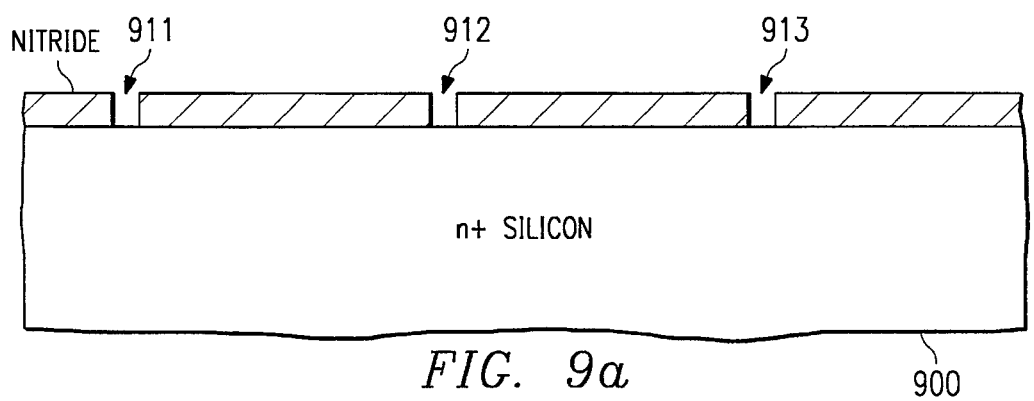
FIGS. 9a–c show fabrication steps in enlarged cross sectional views.
Figure 9B:
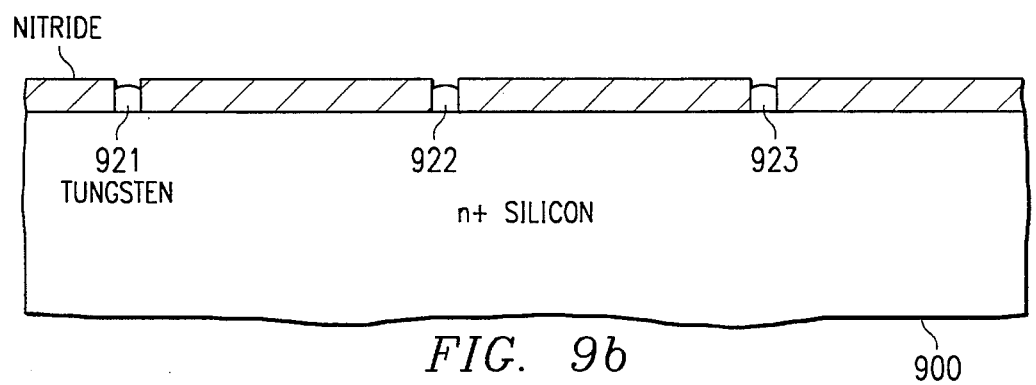
Figure 9C:
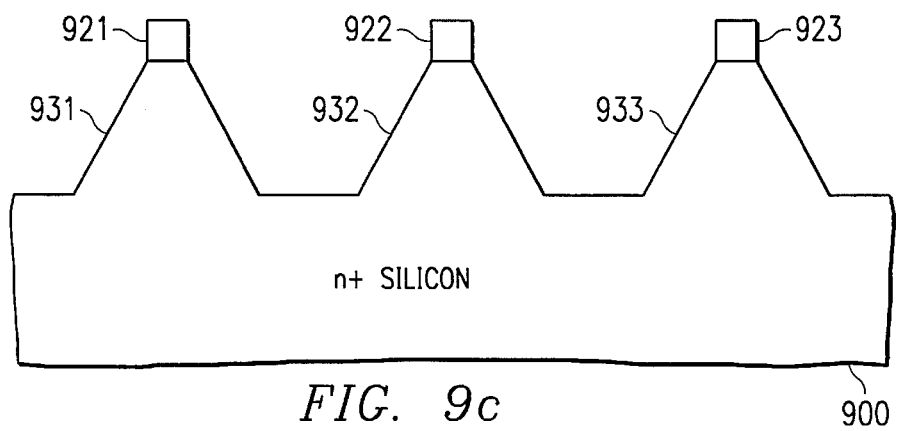

FIGS. 9a–c show the following steps for a method of fabrication of array 800.

(a) Begin with a six-inch diameter n+ silicon wafer 900 having (100) orientation and deposit a nitride (silicon nitride) layer of thickness about 5000 Å. Spin on photoresist and expose and develop a pattern in the photoresist which consists of an array of small openings (0.5 µm by 0.5 µm) spaced about 3 µm apart and with sidewalls parallel to {110} planes which includes the standard wafer flat for (100) wafers. Etch the exposed nitride with hot $H_3PO_4$ using the patterned photoresist as etch mask; then strip the photoresist. There will be some undercutting and the resultant nitride will be an array of small square openings of side about 0.6 µm and spaced about 2.9 µm apart. See FIG. 9a showing nitride openings 911–913.

(b) Deposit a 10,000 Å thick layer of tungsten by chemical vapor deposition; this fills openings 911, 912, 913, . . . and forms an essentially planar surface. Then plasma etch the tungsten with a timed etch to leave openings 911, 912, 913, . . . essentially filled with tungsten plugs 921, 922, 932, . . . but the nitride clear. See FIG. 9b. Alternatively, a thinner (e.g., 1000 Å) layer of tungsten can be vacuum deposited and then electroplated up to the required 10,000 Å thickness.

(c) Strip the nitride using reactive ion etching (RIE) with $CF_4$ plus $O_2$ and then etch the exposed silicon 900 with an ODE such as an aqueous solution of KOH and proponal at 80° C. as in step (b) of the first preferred embodiment. This etch solution etches {111} very slowly and yields small mesas under the tungsten plugs 911–913. The mesas have {111} faces and height dependent upon timing the etch. See FIG. 9c showing mesas 931–933 with toping tungsten plugs 921–923. Of course, if the ODE were allowed to go to completion, then the pyramids 931–933 would have abutting bases and there would be no horizontal surface.

(d) Sharpen the tips of tungsten plugs 921–923 by electrolytic etching to yield array 800 illustrated in FIG. 8. Again, glue array 900 with conductive epoxy into a wrist band holder to complete the ESD system.

Further preferred embodiments

Figure 10:
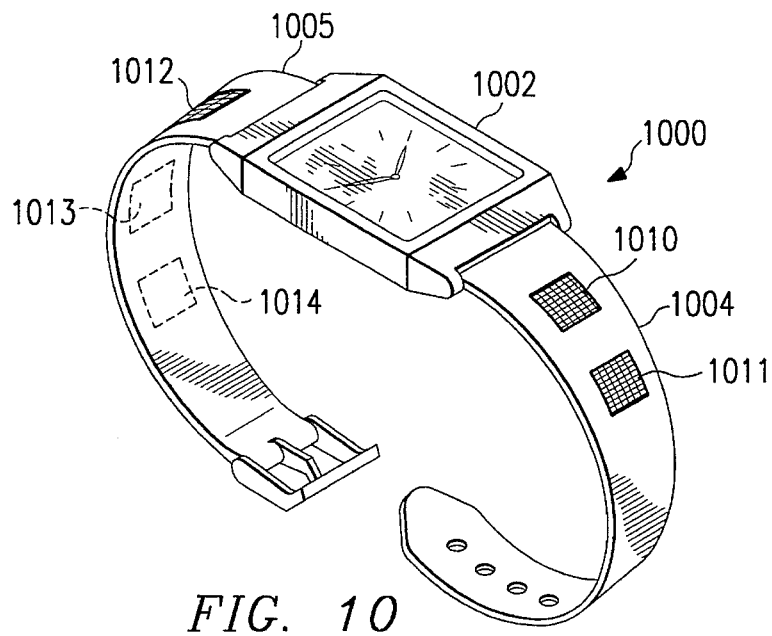
FIGS. 10–11 show further embodiments.

FIG. 10 shows preferred embodiment 1000 as an alternative to embodiment 100 of FIG. 1. In particular, a conventional wrist watch 1002 has detachable, electrically conductive wrist band pieces 1004–1005 which, in turn, contain charbe dissipators 1010–1014. Each charge dissipator may have the structure of charge dissipator 102. System 1000 permits adaptation to an individual's existing wrist watch.

Figure 11:
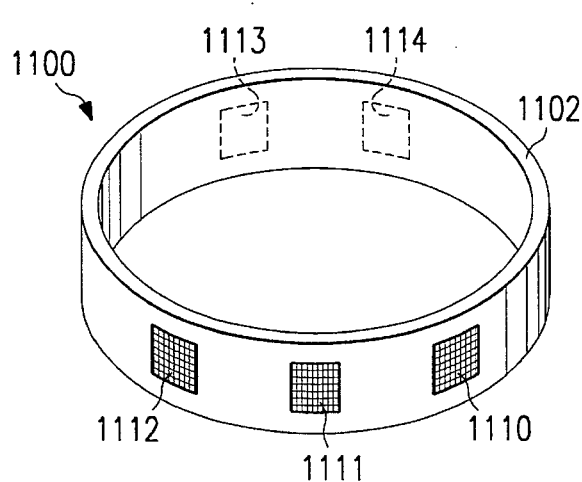

Similarly, FIG. 11 illustrates system 1100 including elastic band 1102 with imbedded charge dissipators 1110–1114. An individual could wear elastic band 1102 around a wrist or around an ankle. Again, each charge dissipator could have the structure of charge dissipator 102. Elastic band 1102 may itself be electrically conductive, or the charge dissipators could protrude through to make contact with an individual's skin. Further, the charge dissipators could have varying orientations so that elastic band 1102 may be reversible but always have at least one charge dissipator operative.

Electron emitter

Figure 12:
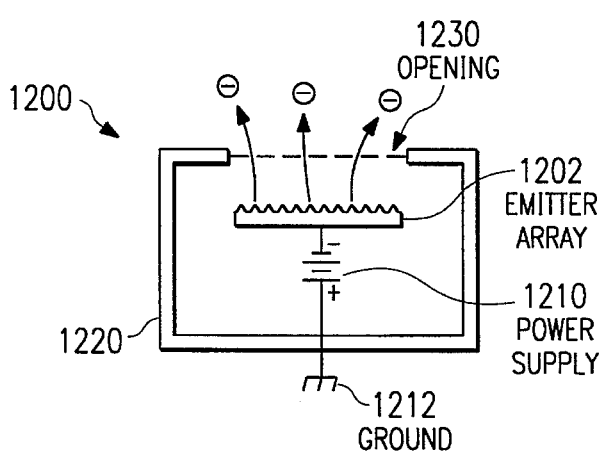
FIG. 12 illustrates an environmental electron emitter.

FIG. 12 is a functional block diagram of preferred embodiment system 1200 which emnits electrons into the environment. Emission of electrons into the ambient creates an electrically conducting atmosphere which both reduces ESD effects and provides for an individual's personal comfort.

System 1200 includes emitter array 1202 analogous to charge dissipator 102 and self-contained power supply 1210 within container 1220 which has an opening 1230 for emission of electrons from array 1202 into the ambient atmosphere. Power supply 1210 could be a battery or an ac-dc converter and powered by 120 volt household power with ground 1212 the wall socket ground. Opening 1230 could be a screened aperture or any electrically translucent aperture. Power supply 1210 could include feedback for voltage regulation and adaptation to ambient conditions.

Modifications and advantages

The preferred embodiments may be varied in many ways while retaining one or more of the features of an array of emitters to provide electric discharge into ambient air.

For example, the array material could be p-type silicon or other doped semiconductors or metals or organic conductors or thin conductive films on insulators and so forth. Other emitter shapes, such as wedges (see Liu et al, 58 Appl. Phys. Lett 1042 (1991)) with sharp corners. Inter-emitter separations could be varied according to the desired number of emitters per unit of area protected. the emitter array need not be physically uniform in layout, and the emitters can be thermally soldered onto their conductive substrate.

The emitter array could be in contact with another part of an individual's body and incorporated into clean room clothing, such as mounted about the ankle or into a cap. Further, moving machinery such as mobile robots or wafer carriers in semiconductor process facilities which may accumulate electrostatic charge could have an attached array of emitters.

The invention has the advantages of reducing ESD effects in a simple manner and emitting electrons in the ambient simply.

What is claimed is:

1. An electrostatic charge dissipation system for attachment to and static electric discharge of a body, comprising:
   (a) a plurality of field emitters; and
   (b) an electrically conductive attachment directly connecting said emitters to said body, whereby electrostatic charge acquired by said body can be dissipated into the ambient atmosphere.

2. The system of claim 1, wherein:
   (a) said body is a human being and said attachment includes a wrist band.

3. The system of claim 2, wherein:
   (a) said wrist band includes a wrist watch.

4. The system of claim 1, wherein:
   (a) said body is a human being and said attachment includes an ankle band.

5. The system of claim 1, wherein:
   (a) said body is a machine.

6. The system of claim 1, wherein:
   (a) said field emitters include projections from a silicon substrate.

7. The system of claim 6, wherein:
   (a) said field emitters are silicon projections with tungsten tips.

8. A method of dissipating electrostatic charge from a body, comprising the steps of:
   (a) providing an electrically conductive attachment for said body; and
   (b) providing a plurality of field emitters directly connected to said attachment.

9. The method of claim 8, wherein:
   (a) said body is a human being and said attachment includes a wrist band.

10. The method of claim 9, wherein:
    (a) said wrist band includes a wrist watch.

11. The method of claim 8, wherein:
    (a) said body is a human being and said attachment includes an ankle band.

12. The method of claim 8, wherein:
    (a) said body is a machine.

13. The method of claim 8, wherein:
    (a) said field emitters include projections from a silicon substrate.

14. The method of claim 13, wherein:
    (a) said field emitters are silicon projections with tungsten tips.

15. An electron emitter, comprising:
    (a) an array of field emitters, said field emitters integrated on a semiconductor die; and
    (b) a power supply to apply a voltage to said field emitters relative to ambient.

16. The emitter of claim 15, wherein:
    (a) said semiconductor is n-type silicon.

17. The emitter of claim 15, wherein:
    (a) said power supply is a battery.

* * * * *